(12) United States Patent
Yüksel et al.

(10) Patent No.: US 8,057,818 B2
(45) Date of Patent: *Nov. 15, 2011

(54) METHODS OF MAKING EXPANDABLE FOAM-LIKE BIOMATERIALS

(75) Inventors: K. Umit Yüksel, Kennesaw, GA (US); Ana T. Bird, Achworth, GA (US); Kirby S. Black, Achworth, GA (US)

(73) Assignee: CryoLife, Inc., Kennesaw, GA (US)

( * ) Notice: Subject to any disclaimer, the term of this patent is extended or adjusted under 35 U.S.C. 154(b) by 1064 days.

This patent is subject to a terminal disclaimer.

(21) Appl. No.: 11/042,181

(22) Filed: Jan. 26, 2005

(65) Prior Publication Data

US 2005/0158364 A1    Jul. 21, 2005

Related U.S. Application Data

(63) Continuation of application No. 09/986,124, filed on Nov. 7, 2001, now Pat. No. 7,226,615.

(60) Provisional application No. 60/246,063, filed on Nov. 7, 2000.

(51) Int. Cl.
  *A61L 15/16* (2006.01)
  *A61K 31/74* (2006.01)
  *A61K 9/14* (2006.01)

(52) U.S. Cl. ............... 424/444; 424/78.06; 424/484

(58) Field of Classification Search ............... None
  See application file for complete search history.

(56) References Cited

U.S. PATENT DOCUMENTS

| | | | |
|---|---|---|---|
| 3,800,792 A * | 4/1974 | McKnight et al. | 602/50 |
| 4,247,406 A | 1/1981 | Widder et al. | |
| 4,309,777 A | 1/1982 | Patil | |
| 4,342,636 A | 8/1982 | Chang et al. | |
| 4,390,450 A * | 6/1983 | Gibson et al. | 516/16 |
| 4,394,370 A | 7/1983 | Jefferies | |
| 4,472,840 A | 9/1984 | Jefferies | |
| 4,522,753 A * | 6/1985 | Yannas et al. | 530/356 |
| 4,620,327 A | 11/1986 | Caplan et al. | |
| 4,623,553 A | 11/1986 | Ries et al. | |
| 4,655,980 A | 4/1987 | Chu | |
| 4,714,469 A | 12/1987 | Kenna | |
| 4,759,766 A | 7/1988 | Buettner-Janz et al. | |
| 4,822,361 A | 4/1989 | Okita et al. | |
| 4,911,718 A | 3/1990 | Lee et al. | |
| 4,970,156 A | 11/1990 | Avrameas et al. | |
| 5,061,383 A * | 10/1991 | Friloux et al. | 252/3 |
| 5,071,437 A | 12/1991 | Steffee | |
| 5,099,003 A | 3/1992 | Kotitschke et al. | |
| 5,132,108 A | 7/1992 | Narayanan et al. | |
| 5,171,574 A | 12/1992 | Kuberasampath et al. | |
| 5,213,580 A | 5/1993 | Slepian et al. | |
| 5,258,028 A | 11/1993 | Ersek et al. | |
| 5,272,074 A | 12/1993 | Rubens | |
| 5,324,647 A | 6/1994 | Rubens et al. | |
| 5,326,568 A | 7/1994 | Giampapa | |
| 5,344,451 A | 9/1994 | Dayton | |
| 5,373,431 A | 12/1994 | Hayman et al. | |
| 5,385,606 A * | 1/1995 | Kowanko | 106/156.3 |
| 5,510,121 A | 4/1996 | Rhee et al. | |
| 5,510,418 A | 4/1996 | Rhee et al. | |
| 5,514,180 A | 5/1996 | Heggeness et al. | |
| 5,529,913 A | 6/1996 | Clayton et al. | |
| 5,549,664 A | 8/1996 | Hirata et al. | |
| 5,584,875 A | 12/1996 | Duhamel et al. | |
| 5,585,116 A | 12/1996 | Boniface et al. | |
| 5,591,224 A | 1/1997 | Schwartz et al. | |
| 5,606,019 A | 2/1997 | Cappello | |
| 5,609,631 A | 3/1997 | Rubens et al. | |
| 5,630,842 A | 5/1997 | Brodniewicz | |
| 5,660,857 A | 8/1997 | Haynes et al. | |
| 5,665,114 A | 9/1997 | Weadock et al. | |
| 5,693,098 A | 12/1997 | Rubens et al. | |
| 5,755,797 A | 5/1998 | Baumgartner | |
| 5,763,411 A | 6/1998 | Edwardson et al. | |
| 5,766,584 A | 6/1998 | Edelman et al. | |
| 5,770,417 A | 6/1998 | Vacanti et al. | |
| 5,773,577 A | 6/1998 | Cappello | |
| 5,817,303 A | 10/1998 | Stedronsky et al. | |

(Continued)

FOREIGN PATENT DOCUMENTS

EP    0 349 505    1/1990

(Continued)

OTHER PUBLICATIONS

The Merck Index, Fourteenth Edition, checked on May 29, 2008.*

(Continued)

*Primary Examiner* — Cherie M Woodward
*Assistant Examiner* — Tigabu Kassa
(74) *Attorney, Agent, or Firm* — Sutherland Asbill & Brennan LLP

(57) ABSTRACT

Liquid, injectable, aqueous solutions are transformed in situ to an expandable foam-like, space filling, and adherent biomaterial. Preferably, the foam-like biomaterial is the reaction product of a two-part liquid system to achieve the in situ formation thereof. The liquid system is generally comprised of a protein solution and a cross linker solution which may either be premixed and then applied to a site in need of the biomaterial, or simultaneously mixed and delivered through an in-line mixing/dispensing tip directly to the site. In especially preferred embodiments, an expandable foam-like biomaterial includes the reaction product of human or animal-derived protein material and a di- or polyaldehyde in the presence of a bicarbonate and an acidic titrant amounts sufficient to impart a cellular foam structure to the material.

26 Claims, No Drawings

U.S. PATENT DOCUMENTS

| | | | |
|---|---|---|---|
| 5,824,093 A | 10/1998 | Ray et al. | |
| 5,827,328 A | 10/1998 | Buttermann | |
| 5,836,313 A | 11/1998 | Perez et al. | |
| 5,865,845 A | 2/1999 | Thalgott | |
| 5,865,846 A | 2/1999 | Bryan et al. | |
| 5,874,500 A | 2/1999 | Rhee et al. | |
| 5,891,558 A * | 4/1999 | Bell et al. | 428/218 |
| 5,900,245 A | 5/1999 | Sawhney et al. | |
| 5,906,997 A | 5/1999 | Schwartz et al. | |
| 5,922,379 A | 7/1999 | Wang | |
| 5,932,659 A | 8/1999 | Bambara et al. | |
| 6,018,030 A | 1/2000 | Ferrari et al. | |
| 6,045,580 A | 4/2000 | Scarborough et al. | |
| 6,051,648 A | 4/2000 | Rhee et al. | |
| 6,099,565 A | 8/2000 | Sakura, Jr. | |
| 6,166,130 A | 12/2000 | Rhee et al. | |
| 6,183,581 B1 | 2/2001 | Ducci et al. | |
| 6,206,921 B1 | 3/2001 | Guagliano et al. | |
| 6,217,603 B1 | 4/2001 | Clark et al. | |
| 6,264,659 B1 | 7/2001 | Ross et al. | |
| 6,264,695 B1 | 7/2001 | Stoy | |
| 6,270,530 B1 | 8/2001 | Eldridge et al. | |
| 6,326,524 B1 | 12/2001 | Fattman et al. | |
| 6,332,894 B1 | 12/2001 | Stalcup et al. | |
| 6,391,049 B1 | 5/2002 | McNally et al. | |
| 6,395,032 B1 | 5/2002 | Gauchet | |
| 6,482,235 B1 | 11/2002 | Lambrecht et al. | |
| 6,488,952 B1 | 12/2002 | Kennedy et al. | |
| 6,589,328 B1 | 7/2003 | Nussinovitch | |
| 6,689,339 B1 * | 2/2004 | Tanaka et al. | 424/44 |
| 6,723,335 B1 | 4/2004 | Moehlenbruck et al. | |
| 6,730,299 B1 * | 5/2004 | Tayot et al. | 424/45 |
| 6,805,697 B1 | 10/2004 | Helm et al. | |
| 6,921,412 B1 | 7/2005 | Black et al. | |
| 6,936,070 B1 | 8/2005 | Muhanna | |
| 6,994,686 B2 | 2/2006 | Cruise et al. | |
| 7,004,945 B2 | 2/2006 | Boyd et al. | |
| 7,183,369 B1 | 2/2007 | Mallapragada et al. | |
| 2004/0220296 A1 | 11/2004 | Lowman et al. | |
| 2006/0089721 A1 | 4/2006 | Muhanna et al. | |
| 2007/0173943 A1 | 7/2007 | Dulak et al. | |
| 2008/0058942 A1 | 3/2008 | Yuksel et al. | |

FOREIGN PATENT DOCUMENTS

| | | |
|---|---|---|
| EP | 0 621 044 A2 | 10/1994 |
| EP | 0968729 A2 | 1/2000 |
| JP | H03-23864 | 1/1991 |
| JP | H03-41952 | 2/1991 |
| JP | 3127709 | 5/1991 |
| JP | H06-30985 | 2/1994 |
| JP | 200079161 | 3/2000 |
| JP | 2001 561372 | 2/2001 |
| JP | 2001 510530 | 7/2001 |
| WO | WO 94/1508 | 1/1994 |
| WO | 9639203 | 12/1996 |
| WO | 98/00180 | 1/1998 |
| WO | 98/02204 A1 | 1/1998 |
| WO | WO 99/09149 | 2/1999 |
| WO | 99/20318 | 4/1999 |
| WO | 00/09018 | 2/2000 |
| WO | 00/33764 | 6/2000 |
| WO | 0045870 | 8/2000 |
| WO | 0047245 | 8/2000 |
| WO | 00/61668 A1 | 10/2000 |
| WO | 00/70018 A1 | 11/2000 |
| WO | 02/34111 A2 | 5/2002 |

OTHER PUBLICATIONS

Frederick C. Mish et al. Webster's ninth new collegiate dictionary, 478, Meriam-Webster Inc., 9th edition, 1990.*

Kai-Uwe et al., Effect of poly(propylene fumarate) foaming cement on the healing of bone defects, Tissue Engineering, 5, 1999.*

SJ He et al; "Silk I Structure in Bombyx Mori Silk Foams"; Int J Biol Macromol. Mar.-Apr. 1999; 24(2-3):187-95; National Library of Medicine PubMed.

Disclosure under 37 C.F.R. 1.56 dated Apr. 23, 2009, filed for U.S. Appl. No. 11/042,180.

Michael Viggiano et al, U.S. Appl. No. 08/191,624, filed Feb. 4, 1994, "Vertebral Interbody Fusion Graft Device & Method of Use,".

Office Action mailed Jun. 24, 2008 corresponding to U.S. Appl. No. 11/008,609.

Supplementary European Search Report EP01273879 dated Sep. 22, 2009.

European Patentability Opinion EPO01273879 dated Mar. 12, 2010.

Chin Koko Hei et al, Collection of Presentations from the 11th Bioengineering Lecture, the Japan Society of Mechanical Engineers, Mar. 24, 1999, pp. 380 and 381 (1999).

Park, S.K., et al., JACOS, 76 (10), pp. 1201 to 1205 (1999).

XP-002217022; Section Ch, Week 198520; Anonymous: "Modification of flexible fabrics, leather and webs—by impregnation with aq. Plastics dispersion and heat coagulation of dispersed plastic"; abstract; & Research Disclosure; vol. 252, No. 029, Apr. 10, 1985 (Apr. 1, 1985), Emsworth, GB.

* cited by examiner

METHODS OF MAKING EXPANDABLE FOAM-LIKE BIOMATERIALS

CROSS-REFERENCE TO RELATED APPLICATION

The present application is a continuation of application Ser. No. 09/986,124 filed Nov. 7, 2011, now U.S. Pat. No. 7,726,615 which in turn is based on, and claims domestic priority benefits under 35 USC §119(e) from, U.S. Provisional Application Ser. No. 60/246,063 filed on Nov. 7, 2000, the entire content of which is expressly incorporated hereinto by reference.

FIELD OF THE INVENTION

The present invention relates generally to the field of biomaterials. More specifically, the present invention relates to biomaterials having foam-like properties and to the in situ methods of making the same.

BACKGROUND AND SUMMARY OF THE INVENTION

Biological and synthetic materials are used conventionally for generating biomaterials that are employed to grow tissue and for achieving hemostasis. For example, U.S. Pat. No. 5,895,412 to Tucker[1] discloses a collagen formulation which, when subject to sufficient elevated temperature, create an effective barrier against blood leaks. U.S. Pat. No. 4,395,396 to Eibl et al. discloses the use of a formulation of blood coagulation factors for hemostasis. Fibrin based materials have also been used as a scaffold for tissue growth (Ye et al, "Fibrin Gel as Three Dimensional Matrix in Cardiovascular Tissue Engineering", European Journal of Cardio-Thoracic Surgery, vol. 17, pages 87-591 (2000)).

[1] The entire disclosure of each U.S. Patent and other publication cited hereinafter is hereby expressly incorporated hereinto by reference.

In order to grow cells, it has been suggested previously that polymer/salt composites be used to make biocompatible porous polymer membranes, particularly resorbable polymers of poly(L-lactic acid) poly (D,L-lactic acid) and poly (D,L-lactic-co-glycolic acid). (See, Mikos et al. U.S. Pat. No. 5,514,378). Collagen and polyglycolic acid mesh have also been disclosed as a means to construct an artificial esophagus. (See, Miki et al, ASAIO Journal, volume 45, pages 502-508 (1999)).

Surgical adhesive compositions for tissue are also well known as evidenced, for example, by U.S. Pat. No. 5,385,606. In general, such surgical adhesives are achieved by combining a two part system typically comprised of a water soluble proteinaceous material (e.g., albumin, particularly bovine or human serum albumin), and a di- or polyaldehyde (e.g., glutaraldehyde) in appropriate amounts, and allowing the combined mixture to react in situ on the tissue surface or surfaces to be bonded. In this manner, sutureless (or minimally sutured) repairs of tissue wounds, perforations, tears and the like may be achieved.

None of the biomaterials used as cell growth matrices, hemostatic agents or surgical adhesives, however, are expandable in situ by the presence of blowing agents to achieve a foam-like structure. Therefore, it is towards providing such biomaterials and methods that the present invention is directed.

Broadly, the invention disclosed herein is embodied in a liquid, injectable, biomaterial that is transformed in situ to a foam-like, space filling, and adherent hydrogel. More specifically, the present invention is embodied in a two-part liquid system to achieve the in situ formation of a foam-like biomaterial. The liquid system is generally comprised of a protein solution and a cross linker solution which may either be premixed and then applied to a site in need of the biomaterial, or simultaneously mixed and delivered through an in-line mixing/dispensing tip directly to the site.

An expandable foam-like biomaterial is formed in response to the respective liquid components in the two-part liquid system being brought into contact with one another. When the two components are mixed with one another, the resulting biomaterial that is formed in situ adheres to virtually any man-made surface (e.g., surfaces formed of plastic, wood, metal, and chamois materials), as well as to human, plant and animal tissue. The resulting biomaterial exhibits the properties of both a closed-cell-foam and open-cell-foam. In this regard, the presence of closed cells is indicated by the ability of the biomaterial to resiliently recover from deformation to its original shape. The presence of open cells is indicated by its ability to absorb and release liquid (e.g., water, physiological buffers and the like). The foam-like biomaterial is soft to the touch and easily compressible.

These and other aspects and advantages will become more apparent after careful consideration is given to the following detailed description of the preferred exemplary embodiments thereof.

DETAILED DESCRIPTION OF THE INVENTION

Virtually any suitable proteinaceous biopolymer may be employed in the practice of the present invention. In this regard, the term "proteinaceous biopolymer" and like terms as used herein and in the accompanying claims mean a polymeric or copolymeric material which contains one or more units in the polymer chain comprised of natural, synthetic or sequence-modified proteins, peptides or polypeptides, and mixtures and blends of such polymeric and/or copolymeric materials.

Most preferably, as noted above, the foam-like biomaterials of the present invention are formed by mixing a two-part liquid system. One especially preferred biopolymer that may be employed in the practice of this invention is a cross-linked reaction product of a two part mixture initially comprised of:

Part A: an aqueous solution comprised of a water-soluble proteinaceous material of about 27-53%, and more preferably about 45%, by weight of the mixture, and up to about 2 moles/liter of a bicarbonate, and Part B: di- or polyaldehydes present in a weight ratio of one part by weight to every 20-60 parts of protein present by weight in the mixture and a titrant, and optionally containing non-essential ingredients to make up the balance of the composition.

Part A of the mixture is most preferably substantially an aqueous solution of a proteinaceous material of human or animal origin which also contains an amount of bicarbonate sufficient to impart a foam-like physical structure to the biomaterial. Albumins including ovalbumins are preferred proteins, and serum albumins of human or animal origin are particularly preferred. The proteinaceous material may be a purified protein or a mixture in which the proteins such as serum albumins are the predominant ingredients. For example, the solid mixtures obtained by dehydration of blood plasma or serum, or of commercial solutions of stabilized plasma proteins, can be used to prepare Part A. These mixtures, generally referred to as plasma solids or serum solids, are known to contain albumins as their major ingredients, of the order of 50-90%. As used herein, the term "plasma" refers to whole blood from which the corpuscles have been removed by centrifugation. The term "serum" refers to plasma which has additionally been treated to prevent agglutination by removal or its fibrinogen and/or fibrin, or by inhibiting the fibrin clot formation through addition of reagents, such as citrate or EDTA.

The pH of the Part A solution may be adjusted to achieve the desired properties. Most preferably, the pH of the Part A solution is neutral or alkaline.

The adhesive properties of the resulting biomaterial are derived from the reaction of the aldehyde with the protein and the surrounding tissue in contact with the biomaterial. In the preferred embodiments of the present invention, the protein is serum albumin (human or animal) or hemoglobin (human or animal), and the aldehyde is glutaraldehyde.

Virtually any technique to impart an internal cellular foam structure to polymeric materials generally may be employed in the practice of the present invention. Thus, for example, gaseous blowing agents, especially inert blowing agents, such as air, nitrogen, argon, carbon dioxide and combinations thereof, may be directly injected into the liquid pre-polymeric material so as to form the desired internal cellular foam structure.

Most preferably, however, when a two part liquid prepolymeric mixture is employed, then an inorganic compound which reacts to evolve a gaseous blowing agent may be incorporated into the individual components prior to mixing. For example, one of the components of the mixture may include a bicarbonate compound while the other component of the mixture may be provided with an acidic titrant in an amount sufficient to cause carbon dioxide gas to be evolved when the two components are mixed together. In such a manner, therefore, the biopolymeric materials of the present invention may be "foamed" in situ, for example, at a tissue site of a patient in need of repair, filling and/or reconstruction.

More specifically, when the two part liquid system described previously is employed in the practice of the present invention, it is preferred that Part A include an amount of a bicarbonate sufficient to impart a foam-like structure to the resulting biomaterial. Inorganic and organic bicarbonates may be employed. Preferred inorganic bicarbonates employed in the practice of the present invention include metal bicarbonates, such as bicarbonates of sodium, potassium, aluminum, iron and the like. Especially preferred inorganic bicarbonates are sodium and potassium bicarbonates. A preferred inorganic bicarbonate includes ammonium bicarbonate. The amount of water in the Part A solution is adjusted as needed.

Part B of the two-part liquid system employed in the practice of the present invention may therefore be substantially an aqueous solution comprised of di- or polyaldehydes and a titrant. A wide range of di- or polyaldehydes exist, and their usefulness is restricted largely by availability and by their solubility in water. For example, aqueous glyoxal (ethandial) is useful, as is aqueous glutaraldehyde (pentandial). Water soluble mixtures of di- and polyaldehydes prepared by oxidative cleavage of appropriate carbohydrates with periodate, ozone or the like are also useful. Glutaraldehyde is the preferred dialdehyde ingredient of Part B.

A titrant is most preferably employed in the liquid solution of Part B. More specifically, the titrant is an organic or inorganic acid, buffer, salt, or salt solution which is capable of reacting with the bicarbonate component of Part A to generate carbon dioxide ($CO_2$) and water as reaction by-products. The carbon dioxide gas that is generated creates the foam-like structure of the resulting biomaterial and also causes the volume of the biomaterial to expand greater than the sum of the volume of individual Part A and Part B components mixed together.

Most preferably, the titrant is an inorganic or organic acid that is present in an amount to impart an acidic pH to the resulting mixture of the Part A and Part B components. Preferred acids that may be employed in the practice of the present invention include phosphoric acid, sulfuric acid, hydrochloric acid, acetic acid and citric acid.

The proteinaceous biopolymeric materials in accordance with the present invention may be provided with an open cell, closed cell or combination of open and closed cell structure. In this regard, the particular cellular foam structure that may be provided is dependent on the amount of the gaseous blowing agent that is employed during the foaming process. Thus, for example, when the gaseous blowing agent is an inorganic bicarbonate that evolves carbon dioxide gas, the amount of evolved gas may be achieved by controllably altering the pH of the mixture (e.g., by use of buffering agents and/or by the relative amounts of the bicarbonate and/or acidic titrant employed) and/or by controllably altering the amount of individual components in the mixture (e.g., by changing the amount of inorganic bicarbonate that may be present).

The amount of gas that is evolved and/or introduced into the liquid pre-polymeric material will also determine the extent to which the resulting solid foamed biomaterial expands. Thus, by controllably altering the pH of the liquid pre-polymeric mixture containing an inorganic blowing agent, it has been found that volume expansions (as compared to the volumes of the non-foamed material) may be controllably altered.

Additionally or alternatively, the pH and/or components of the mixture may be adjusted so as to delay the onset of foaming. For example, with one of the components (e.g., Part B of the cross-linkable biopolymeric mixture described previously) at a pH which is less acidic, (e.g., at pH ranges of at least about 2.0, and up to about 5.0) it has been found that foaming may be delayed for several seconds (e.g., up to about 5 seconds). On the other hand, under more acidic pH conditions (e.g., Part B at pH of less than about 2.0, and typically less than about 1.0), little if any delay in the foaming process ensues.

Delayed foaming may be advantageous for the purpose of allowing delivery of the two part liquid mixture to a site in need of the same (e.g., an injured tissue site in need of repair) so that the biomaterial foaming occurs substantially entirely at the desired site and not within any delivery device or system that may be employed. In addition, delayed foaming may be advantageous to control the cellular pore size and/or structure in that some cross-linkage of the biomaterial may occur prior to foaming.

Whether the gaseous blowing agent is evolved by virtue of the reaction between a solid blowing agent and an acidic titrant or whether a normally gaseous blowing agent is injected directly into the pre-polymeric mixture, it has been found that the amount of gas needed to expand the volume of the foamed biomaterial as compared to the volume of the non-cellular (non-foamed) material will cause the biomaterials of this invention to exhibit a more or less open cellular structure. Thus, at relatively low volumetric expansions, the biomaterials of the present invention will exhibit predominantly (if not entirely) a closed cell structure. On the other hand, at relatively higher volumetric expansions, the biomaterials of the present invention will exhibit predominantly (if not entirely) an open cell structure.

The proteinaceous biomaterials in accordance with the present invention may also integrally include reinforcing media, such as biocompatible fibrous or particulate materials, such as described more fully in copending and commonly owned U.S. patent application Ser. No. 09/570,600 filed on May 12, 2000 (the entire content of which is expressly incorporated hereinto by reference). If used, the fibrous reinforcing media may be in the form of individual fibers, filaments, rovings and/or yarns embedded into the biopolymeric materials. Alternatively (or additionally), the fibrous reinforcing media may be in the form of woven or non-woven fabric or web structures which are embedded physically within the biopolymeric materials. The reinforcing media may also be in the form of particulate media that may be used alone or in combination with the fibrous reinforcing media.

As noted above, the biomaterials in accordance with the present invention exhibit exceptional adhesion properties. Thus, the adhesion of the biomaterials of the present invention may be advantageously employed so as to form composite structures with one or more other component materials. That is, the cellular foam proteinaceous biomaterials of the present invention may be formed as a composite with one or more layers or structural members comprised of non-foam biomaterials of either the same or similar proteinaceous biopolymeric material. In such a situation, the biomaterials will be chemically or ionically bound to one another. Alternatively (or additionally), the biomaterials of the present invention may be adhered to metal, plastic or ceramic structures as may be desired or needed for particular end-use applications. The biomaterials of the present invention also exhibit exceptional adhesion properties to living tissue and may thus be employed advantageously to repair damaged tissue sites.

The two components that form the liquid pre-polymeric materials of this invention are conveniently provided in the form of a kit. That is, the individual components may be provided within separate chambers of a delivery device that allow mixing of the components just prior to use. For example, an attending physician my employ a kit in accordance with the present invention so as to repair damaged tissue of a patient by expelling the two individual components from the kit thereby mixing the components and causing the biomaterial to foam in situ as has been described previously. The kit may thus be pre-sterilized by subjecting it to sufficient sterilizing gamma radiation which will allow the components to be delivered to the tissue in a sterile condition. Moreover, such sterilization will not deleteriously affect the inherent shelf life of the components (which is typically at least about 24 months).

The present invention will be further understood by reference to the following non-limiting Examples.

EXAMPLES

Example 1

Solutions of Part A and Part B were contained in separate chambers of a delivery device. When the device was triggered, the two parts were expelled from their respective chambers into a mixing tip that combined the two solutions and mixed them as they traveled over the static mixing elements present in the tip. Part A was 45% bovine serum albumin solution by weight containing 1.5 molar sodium bicarbonate. Part B was 10% glutaraldehyde containing 3.7 molar phosphoric acid. The ratio of Part A to Part B was 4:1. The material was dispensed into Petri dishes made from polystyrene containing a wooden stick. A foam-like material was formed immediately that expanded. The material polymerized into a solid but flexible, sponge-like texture within about 10 seconds. The material adhered to the dish as well as to the wooden stick therein.

Example 2

The experiment in Example 1 was repeated, except the phosphoric acid concentration was 2 molar.

Example 3

Ten milliliters of the formulation described in Example 1 was dispensed into two 50 ml graduated, polypropylene centrifuge tubes. The material completely filled both containers it was injected into and polymerized in place. It also adhered to the sides of the centrifuge tubes.

Example 4

The formulation described in Example 1 was dispensed separately into the fingers of a latex examination glove. As the material expanded and polymerized, it stretched the latex glove, and the polymerized material conformed to the shape of the glove, which in this case served as a mold. Once the material was polymerized, it could be easily peeled off the glove-mold.

Example 5

The formulation described in Example 1 was dispensed onto synthetic vascular grafts made out of polyester (Dacron®) or expanded polytetrafluoroethylene (Gortex®). In both cases, the material adhered to the synthetic graft material.

Example 6

The formulation described in Example 1 was dispensed between two glass plates about 2.1 mm apart using a needle attached to the dispensing tip. The glass plates were held apart using glass spacers and held together by gravity. The dispensed material filled the void space. After polymerization of about 1 minute, the spacers were removed, and the top glass lifted. It was observed that the biomaterial had adhered to both glass surfaces.

Example 7

The formulation described in Example 1 was dispensed onto a piece of moist chamois cloth of the type marketed for general car-cleaning purposes. Another piece of chamois cloth was then placed immediately thereon. The biomaterial adhered both pieces of the chamois cloth together.

Example 8

Example 1 was repeated, except the bicarbonate used was 1.0 M ammonium bicarbonate.

Example 9

The formulation described in Example 1 was modified to contain varying amounts of sodium bicarbonate in Part A and the corresponding amounts of titrant in Part B. Concentrations of sodium bicarbonate tested were 0.25, 0.5, 0.75, 0.9 and 1.5 molar. In all cases the biomaterial polymerized and formed a foam-like structure.

Example 10

The experiment in Example 1 was repeated except the formulation contained 2 molar sulfuric acid instead of phosphoric acid. The biomaterial polymerized and formed a foam-like consistency.

Example 11

The experiment in Example 6 was repeated using the formulation in Example 9. The biomaterial adhered both pieces of chamois together.

Example 12

The experiment in Example 1 was repeated except the formulation contained 2 molar hydrochloric acid instead of phosphoric acid. The biomaterial polymerized and formed a foam-like consistency.

Example 13

The experiment in Example 1 was repeated except the formulation contained 2 molar acetic acid instead of phosphoric acid. The biomaterial polymerized and formed a foam-like consistency.

Example 14

The experiment in Example 1 was repeated except the formulation contained 2 molar citric acid instead of phosphoric acid. The biomaterial polymerized and formed a foam-like consistency.

Example 15

The experiment in Example 1 was repeated, except in this example, prior to dispensing the mixture, the material was first subjected to gamma irradiation of 35 kGy to sterilize the device. When the contents of the sterilized device was expressed it formed a foam-like, hydrogel biomaterial that was adherent.

Example 16

The experiment in Example 1 was repeated. The polymerized foam-like hydrogel biomaterial was placed into distilled water in a plastic jar. After 52 days the biomaterial was still in one piece and acted like a sponge, being able to absorb and release liquid and to resiliently recover its original shape following deformation.

Example 17

A biopolymeric material was formed by mixing 1.2 M sodium phosphate buffer in 10% glutaraldehyde (pH=4.03) and 0.5 M $NaHCO_3$ in 45% bovine serum albumin. A delay in foaming of the mixture of between about 3-4 seconds was observed.

Example 18

Example 17 was repeated except that 1.5 M acetic acid was employed instead of the phosphate buffer to achieve a pH of 2.17. A delay in foaming of the mixture of between about 1-2 seconds was observed.

Example 19

Example 17 was repeated except that 2 M phosphoric acid was employed instead of the phosphate buffer to achieve a pH of 0.81. No foaming delay was observed.

Example 20

A biopolymeric material was formed by mixing 0.5M $NaHCO_3$ in 45% bovine serum albumin and 10% glutaraldehyde in 0.25M $H_3PO_4$ (pH=1.65). A volume expansion of 2.4 times the original volume of the non-foamed material was observed.

Example 21

Example 20 was repeated except that 2M $H_3PO_4$ was used to achieve a pH of 0.81. A volume expansion of 8 times the original volume of the non-foamed material was observed.

Example 22

Example 20 was repeated except that 1M of $CH_3COOH$ was used instead of $H_3PO_4$ to achieve a pH of 2.38. A volume expansion of 3.4 times the original volume of the non-foamed material was observed.

Example 23

Example 20 was repeated except that 2M of $CH_3COOH$ was used instead of $H_3PO_4$ to achieve a pH of 2.19. A volume expansion of 9 times the original volume of the non-foamed material was observed.

Example 24

A biopolymeric material was formed by mixing 1.33 M sodium phosphate buffer in 10% glutaraldehyde (pH=3.5) and 0.25M $NaHCO_3$ in 45% bovine serum albumin. Very delayed foaming or no foaming was observed.

Example 25

Example 25 was repeated except the pH was adjusted to 0.5. No delay in foaming was observed.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of making a biopolymeric material having a cellular foam structure comprising: combining a proteinaceous pre-polymeric liquid material and a cross linker solution to produce a mixture, wherein the proteinaceous pre-polymeric liquid material comprises a water soluble or plasma protein; introducing or producing a gaseous blowing agent into the proteinaceous pre-polymeric liquid material or the mixture; and allowing the mixture to cross-link and solidify simultaneously with the introduction or production of the gaseous blowing agent to thereby form the biopolymeric material having a cellular foam structure.

2. The method of claim 1, wherein the proteinaceous pre-polymeric liquid material comprises an aqueous solution of human or animal-derived protein material and the cross linker solution comprises an aqueous solution of a di- or polyaldehyde.

3. The method of claim 2, wherein the aqueous solution of human or animal-derived protein material further comprises a bicarbonate and the aqueous solution of said di- or polyaldehyde further comprises an acidic titrant.

4. The method of claim 2 or 3, wherein the biopolymeric material has a volume which is greater than combined volumes of the aqueous solutions.

5. The method of claim 2, wherein the aqueous solution of human or animal-derived protein material is neutral or slightly alkaline.

6. The method of claim 5, wherein the aqueous solution of di- or polyaldehyde is acidic.

7. The method of claim 2, wherein the human or animal-derived protein material comprises albumin.

8. The method of claim 7, wherein the human or animal-derived protein material comprises serum albumin.

9. The method of claim 2, wherein the aqueous solution of a di- or polyaldehyde comprises glutaraldehyde.

10. The method of claim 1, wherein the biopolymeric material is adhesive to human or animal tissue.

11. The method of claim 1, wherein the step of combining comprises:
expelling the proteinaceous pre-polymeric liquid material from a first chamber and expelling the cross linker solution from a second chamber, and
passing the expelled materials into a mixing tip comprising static mixing elements that cause the proteinaceous pre-polymeric liquid material and the cross linker solution to combine to form the mixture.

12. A method of making a biopolymeric material having a cellular foam structure comprising: combining a proteinaceous pre-polymeric liquid material and an aqueous solution of a di- or polyaldehyde to produce a mixture; introducing or producing a gaseous blowing agent into the mixture; and then allowing the mixture to solidify to thereby form the biopolymeric material having a cellular foam structure, wherein the biopolymeric material has a volume which is greater than the sum of the volumes of the proteinaceous pre-polymeric liquid material and aqueous solution.

13. The method of claim 12, wherein the biopolymeric material is adhesive to human or animal tissue.

14. The method of claim 12, wherein the proteinaceous pre-polymeric liquid material comprises human or bovine serum albumin.

15. The method of claim 12, wherein the aqueous solution of a di- or polyaldehyde comprises glutaraldehyde.

16. A method of making a biopolymeric material having a cellular foam structure comprising:
preparing a two-part mixture which comprises a Part A and a Part B, wherein the Part A includes an aqueous solution of a human- or animal-derived protein material and a bicarbonate compound, and the Part B includes an aqueous solution of a di- or polyaldehyde and a titrant, and wherein the bicarbonate compound and the titrant react to evolve a gas into the two-part mixture; and
allowing the two-part mixture to react and solidify, thereby forming a biopolymeric material having a cellular foam structure which has a volume that is greater than the sum of the volumes of the aqueous solutions of Parts A and B.

17. The method of claim 16, wherein the bicarbonate compound comprises sodium bicarbonate, potassium bicarbonate, or ammonium bicarbonate.

18. The method of claim 16, wherein the titrant comprises phosphoric acid, sulfuric acid, hydrochloric acid, citric acid, or acetic acid.

19. The method of claim 16, wherein the human- or animal-derived protein material comprises albumin.

20. The method of claim 19, wherein the albumin is human or bovine serum albumin.

21. The method of claim 16, wherein the di- or polyaldehyde comprises a glutaraldehyde.

22. A foam biomaterial comprising: a human- or animal-derived plasma or water-soluble protein material crosslinked with a di- or polyaldehyde, wherein the di- or polyaldehyde comprises glutaraldehyde, wherein the biomaterial comprises a solid cellular foam structure comprising albumin, and wherein the foam biomaterial is sterilized.

23. The biomaterial of claim 22, which is made by the method of claim 2.

24. The biomaterial of claim 22, wherein the albumin comprises human or bovine serum albumin.

25. The biomaterial of claim 22, wherein the cellular foam structure comprises both open and closed cells.

26. The biomaterial of claim 22, which is adhesive to human or animal tissue.

* * * * *